(12) United States Patent
Aemmer

(10) Patent No.: US 6,243,166 B1
(45) Date of Patent: Jun. 5, 2001

(54) PROCESS AND DEVICE FOR RECOGNITION OF FOREIGN BODIES IN FIBRE OF PREDOMINANTLY TEXTILE FIBRES

(75) Inventor: Peter F. Aemmer, Wettswil (CH)

(73) Assignee: Zellweger Luwa AG, Uster (CH)

( * ) Notice: Subject to any disclaimer, the term of this patent is extended or adjusted under 35 U.S.C. 154(b) by 0 days.

(21) Appl. No.: 09/214,582
(22) PCT Filed: Jun. 26, 1997
(86) PCT No.: PCT/CH97/00253
  § 371 Date: Dec. 31, 1998
  § 102(e) Date: Mar. 31, 1999
(87) PCT Pub. No.: WO98/00243
  PCT Pub. Date: Jan. 8, 1998

(30) Foreign Application Priority Data

Jul. 2, 1996 (CH) .................................................. 1652/96

(51) Int. Cl.⁷ ........................... G01N 21/84; G01N 21/00
(52) U.S. Cl. ...................... 356/430; 356/429; 356/238.1; 356/238.3
(58) Field of Search ..................................... 356/429, 430, 356/431, 238.1

(56) References Cited

U.S. PATENT DOCUMENTS 5,544,090 * 8/1996 Shofner et al. ...................... 356/430

FOREIGN PATENT DOCUMENTS 44 15 907 * 11/1995 (DE) .
0 233 446 * 5/1987 (EP) .
0 226 430 * 6/1987 (EP) .

* cited by examiner

Primary Examiner—Frank G. Font
Assistant Examiner—Roy M. Punnoose
(74) Attorney, Agent, or Firm—Burns, Doane, Swecker & Mathis, L.L.P.

(57) ABSTRACT

The invention relates to a method and a device for detecting impurities (F) in a fiber stream (1) of mainly textile fibers, wherein the fiber stream and at least one reference quantity (15) are artificially visually sensed. To enable even impurities which are difficult to detect to be removed with improved efficiency, the reference quantity is to be adapted at least periodically.

16 Claims, 5 Drawing Sheets

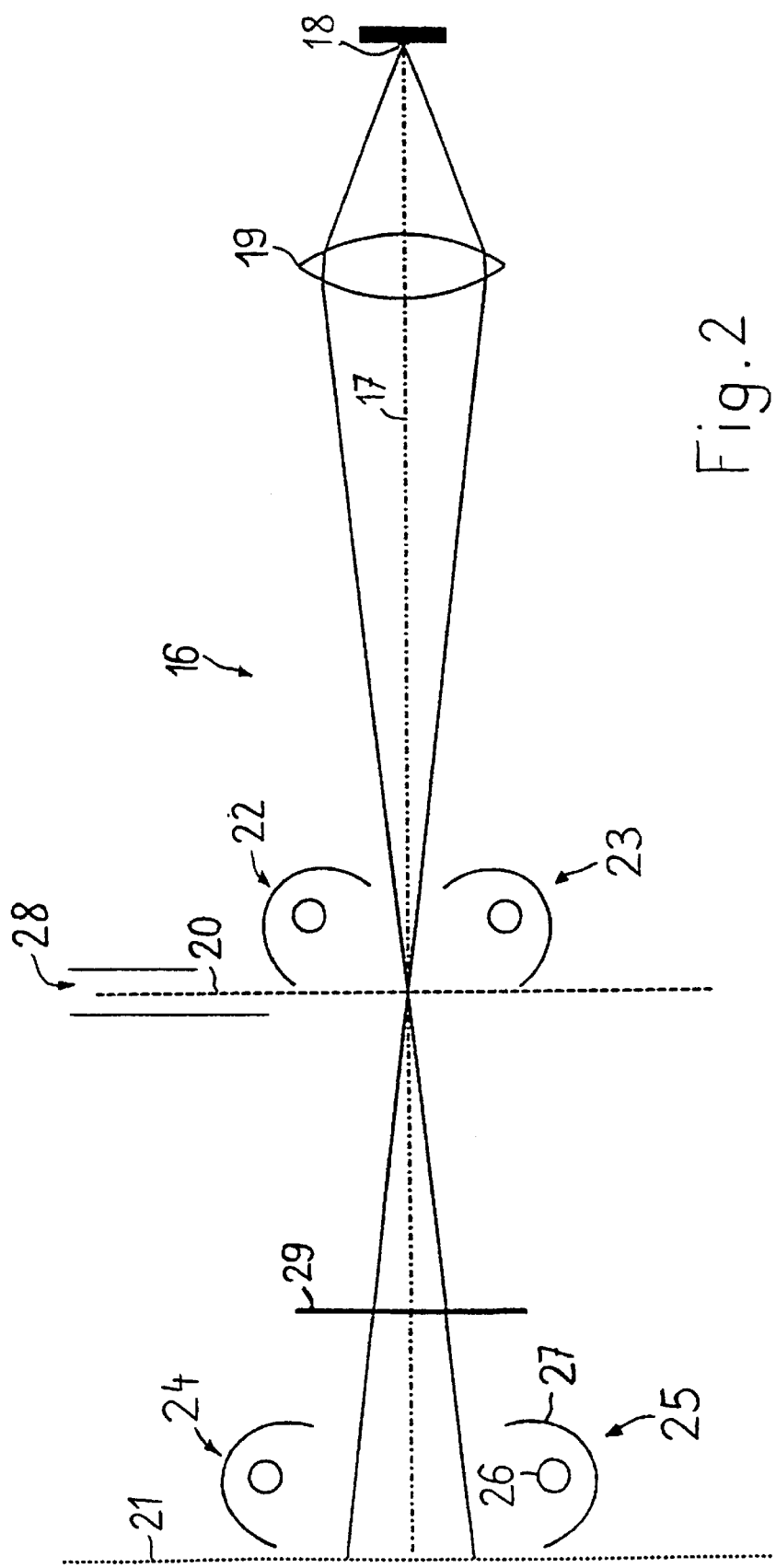

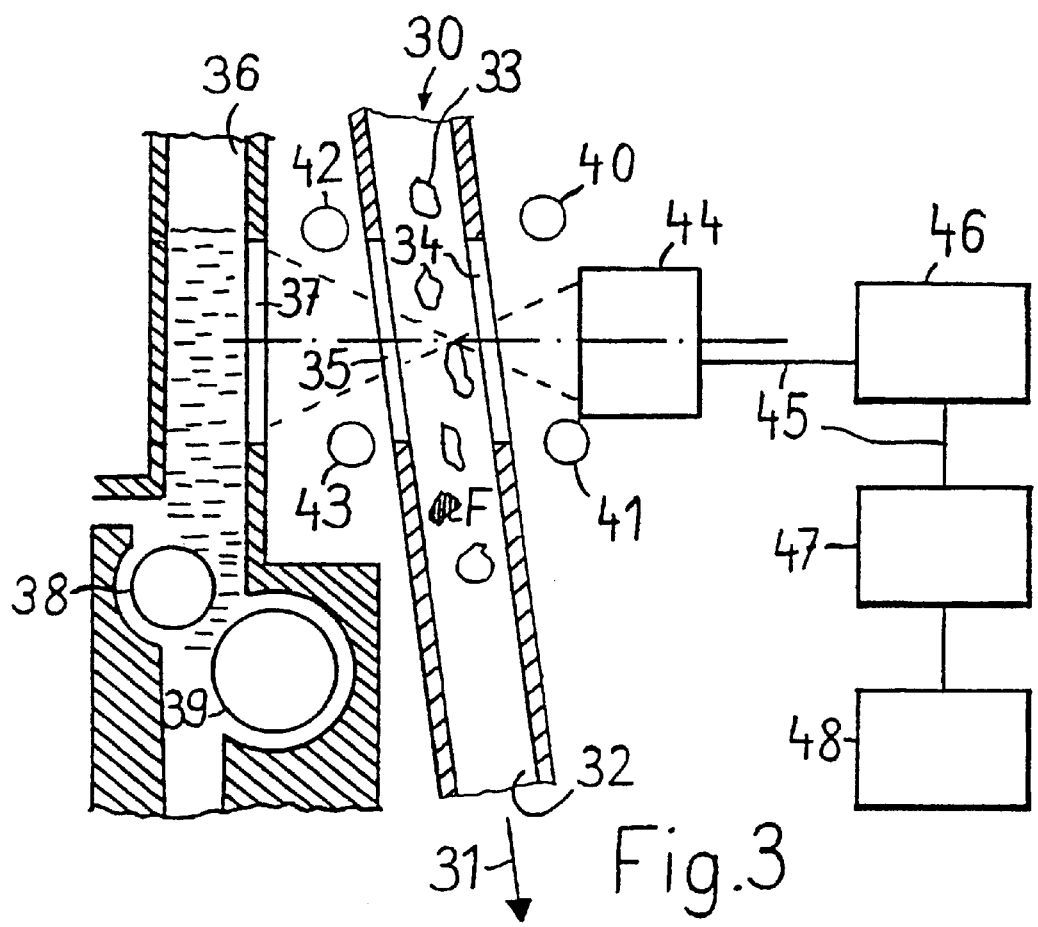
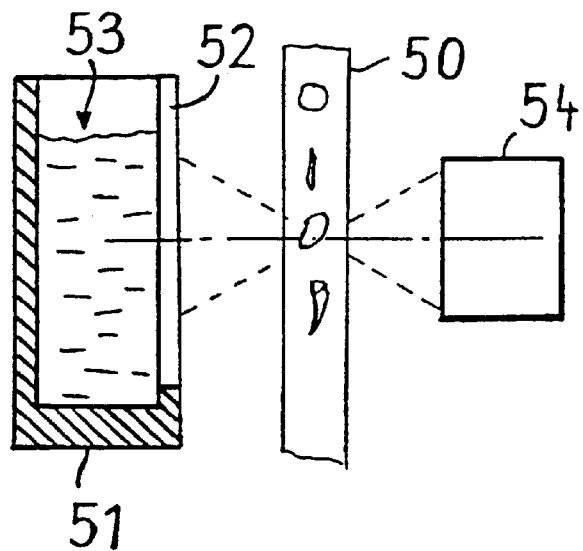

PROCESS AND DEVICE FOR RECOGNITION OF FOREIGN BODIES IN FIBRE OF PREDOMINANTLY TEXTILE FIBRES

The invention relates to a method and a device for detecting impurities in a loosened fiber stream of mainly textile fibers, wherein the fiber stream and at least one reference quantity are artificially visually sensed.

BACKGROUND OF THE INVENTION

From DE-A-4340165 and DE-A-4340173 such methods are known, by means of which, for example, cotton or wool in the form of flocks polluted to a greater or lesser extent with impurities may be freed of said impurities. With said methods it is possible to distinguish between external impurities, which relate to different material, and internal impurities, which relate to the same material but in a different state or a different color. Internal impurities are, for example, cotton or woollen fibers which are partially rotten, agglutinated or contaminated. External impurities are stones, soil, glass, stalk residues, leaves, packaging material, hair, feathers etc. Whereas crude impurities are removed in the known spinning preparation devices, impurities which are more difficult to separate are, according to the known methods, to be detected and removed from the stream of loose material. To said end, the fibers or flocks are conveyed continuously past color sensors which are to detect impurities. Material containing constituents, to which the color sensors have responded, is then removed.

A perceived drawback of such known methods is that many impurities are not detected thereby. one reason is, for example, that impurities, in order to be detected, have to vary in color to a relatively great extent from the textile fibers or the background, which is not always the case. Such known methods do not operate very selectively.

SUMMARY OF THE INVENTION

An object of the present invention is to provide a method and apparatus which allow impurities, which are difficult to separate, to be detected in the fiber stream with greater efficiency.

The object is achieved in that the fiber stream is artificially visually sensed together with a reference quantity, which is adapted at least at intervals or from time to time. This may be effected on the one hand in that the fiber stream, which is to be opened into flocks or into individual fibers, is to be sensed against a background, which is likewise formed by the fiber stream and acts as a reference quantity. On the other hand, the reference quantity may be formed, for example, also by a background which is periodically or continuously adapted to the material to be measured. A possible construction comprises, for example, a channel for a loosened fiber stream and a channel, arranged parallel thereto, for a retained fiber stream. The channel for the loosened fiber stream is to be permeable to light and the channel for the retained fiber stream is to be permeable to exactly the same light at one side. The loosened fiber stream is then sensed or viewed against the background of the retained part of the same stream or of a further fiber stream.

The advantages achieved by the invention are in particular that the comparison process or processes, which precede a decision about the absence or presence of impurities, automatically adapt continuously to the true conditions of the fibers carried along in the fiber stream. The adaptability is to be regarded as stable and robust so long as the precondition is met that, from a statistical viewpoint, impurities are rare in comparison to good fiber material. The same advantages are achieved when a fiber stream, which has already been cleaned and freed of impurities, is used as a reference quantity.

BRIEF DESCRIPTION OF THE DRAWINGS

There follows a detailed description of the invention by way of example and with reference to the accompanying drawings. The drawings show:

FIG. 2 is a simplified view of basic structural features of the device; and

FIGS. 3 to 6 are simplified views of further embodiments of the device according to the invention.

DETAILED DESCRIPTION OF THE INVENTION

Figure 1:
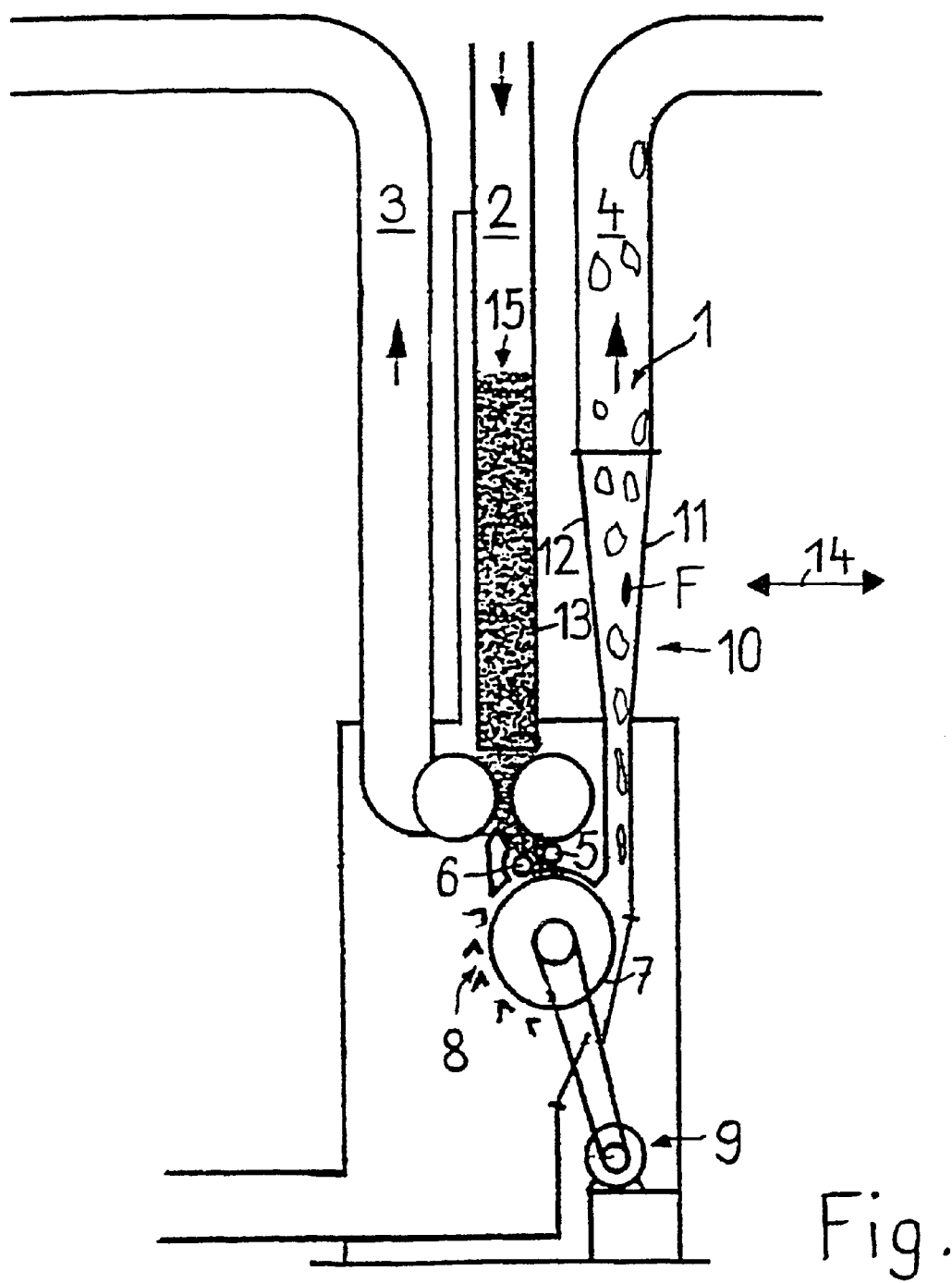
FIG. 1 is a diagrammatic view of a device according to the invention.

FIG. 1 shows, by way of example, part of a cleaning machine for flocks which produces a highly loosened fiber stream 1. The machine comprises, for example, a retaining channel 2, an exhaust air channel 3 and a channel 4 for cleaned flocks or fibers. Also shown are two small feed rollers 5 and 6, a cleaning roller 7, a cutter screen 8 and a drive 9 for the feed rollers 5, 6 and the cleaning roller 7. To said extent, the machine is a known cleaning machine. In one region 10, however, the retaining channel 2 and the channel 4 are each provided with a window 11, 12, 13 so that said channels are permeable to light in the direction of a double arrow 14, i.e. are, for example, of a transparent design. Said arrangement is used to enable sensing of the fiber stream 1 in the channel 4 from the direction of the arrow 14, e.g. by means of a sensor. For said purpose, the retained fibers 15 in the retaining channel 2 form a background or even a reference quantity for the flocks or fibers in the fiber stream 1, which reference quantity is continuously adapted at least at intervals or, in the present case, by the slow, continuous forward motion of the fibers 15.

FIG. 2 shows in a simplified manner a path of rays 16 such as arises during the detection of impurities in the device according to FIG. 1 and also in the devices to be described below. Disposed along an optical axis 17 are a line or point sensor 18, an objective 19, a foreground or object surface 20 and a background 21 or reference surface. Disposed as light sources on both sides of the optical axis 17 in front of the foreground 20 and in front of the background 21 are, for example, gaseous discharge tubes or tubular incandescent lamps with approximately elliptical reflectors 22, 23, 24 and 25. One tubular light source 26 lies in each case at a focal point of the ellipse of the associated reflector 27, while the other focal point is situated in such a way that the background 21 is uniformly lit. The light sources 22, 23 and 24, 25 are all of an identical design and are intended to illuminate the foreground 20 and the background 21 equally brightly. According to FIG. 1, the object surface 20 lies approximately in the center plane of the channel 4, while the background 21 lies approximately in the window 13 of the side wall of the retaining channel 2. The depth of focus is preferably so great that, instead of the object surface, it is possible to talk of an object zone 28 which corresponds approximately to the depth of a channel for the flock flow. By means of the illustrated path of rays 16, the object zone 28 is imaged in a clearly defined manner and the background is imaged in a poorly defined, indistinct manner on the point or line sensor 18. A diffusing screen 29 may optionally also be disposed in the path of rays 15 between the object zone 28 and the background 21. The understanding is that, in the practical realization, a plurality of point sensors forming a line or a plurality of point or line sensors forming a field is provided.

FIG. 3 shows a further device for detecting impurities in a fiber stream. A loosened fiber stream 30, which in the present case comprises fibers combined into flocks 33 and conveyed preferably pneumatically, e.g. in a laminar air flow, more or less loosely in the direction of an arrow 31, is fed in a channel 32. In said flow there are possibly also impurities F. The channel 32 has two windows 34, 35 lying opposite one another. Disposed next to or behind the channel 32 is a further channel 36 with a window 37. The windows 34, 35 and 37 are positioned relative to one another in such a way as to afford a view through the channel 32 into the channel 36. In the channel 36, flocks or fibers are retained in front of the window 37. Feed rollers 38, 39 are also used to control the flow of the retained fibers in the channel 36 in such a way that there are always fibers behind the window 37. Disposed in front of the channels 32 and 36 are, in each case, two light sources 40, 41 and 42, 43 which may, for example, take the form of standard tubular light sources and are used to illuminate the fiber streams behind the transparent windows 34 and 37 in the channels 32 and 36 in a uniform, equally powerful, shadow-free manner. A sensor 44 which may be a camera, for example, has a view through the channel 32 into the channel 36. Thus, the window 34 forms a first location for acquiring measured values and the window 37 forms a second location for acquiring mean values or reference quantities from a fiber stream. The sensor 44 is connected by a line 45 or a bus to an evaluation unit 46, which in turn is connected to a data output unit 47 such as, for example, a visual display unit or printer and to a data input unit 48 such as, for example, a keyboard. The evaluation unit 46 may, for example, comprise an image processing system which, on the basis of statistical features, further improves the differentiation between impurities and flocks. A line sensor may be provided for sensing radiation which is reflected or diffused by the fiber stream in the channel 32. The sensor 44, the evaluation unit 46, the data output unit 47 and the data input unit 48 are elements which are known as such and therefore not shown in greater detail here.

FIG. 4 shows a further construction of the device, in which however only one channel 50 is provided. Here, instead of the channel 36 (FIG. 3), a container 51 is provided which is filled with textile fibers corresponding to fibers in the channel 50. Said container 51 is designed so as to be transparent or open by means of a window 52 in the direction of the channel 50 and serves as a background for viewing the flock stream in the channel 50. The container 51 or its contents 53 may be periodically exchanged in order to adapt the background to variations in the flock stream in the channel 50 which are not to be detected as impurities. Also shown here is a sensor 54 for sensing the flock stream in the channel 50 using the contents 53 as a reference quantity. As contents 53, fibers or flocks are conceivable, which contain impurities or from which the impurities have already been removed.

Figure 5:
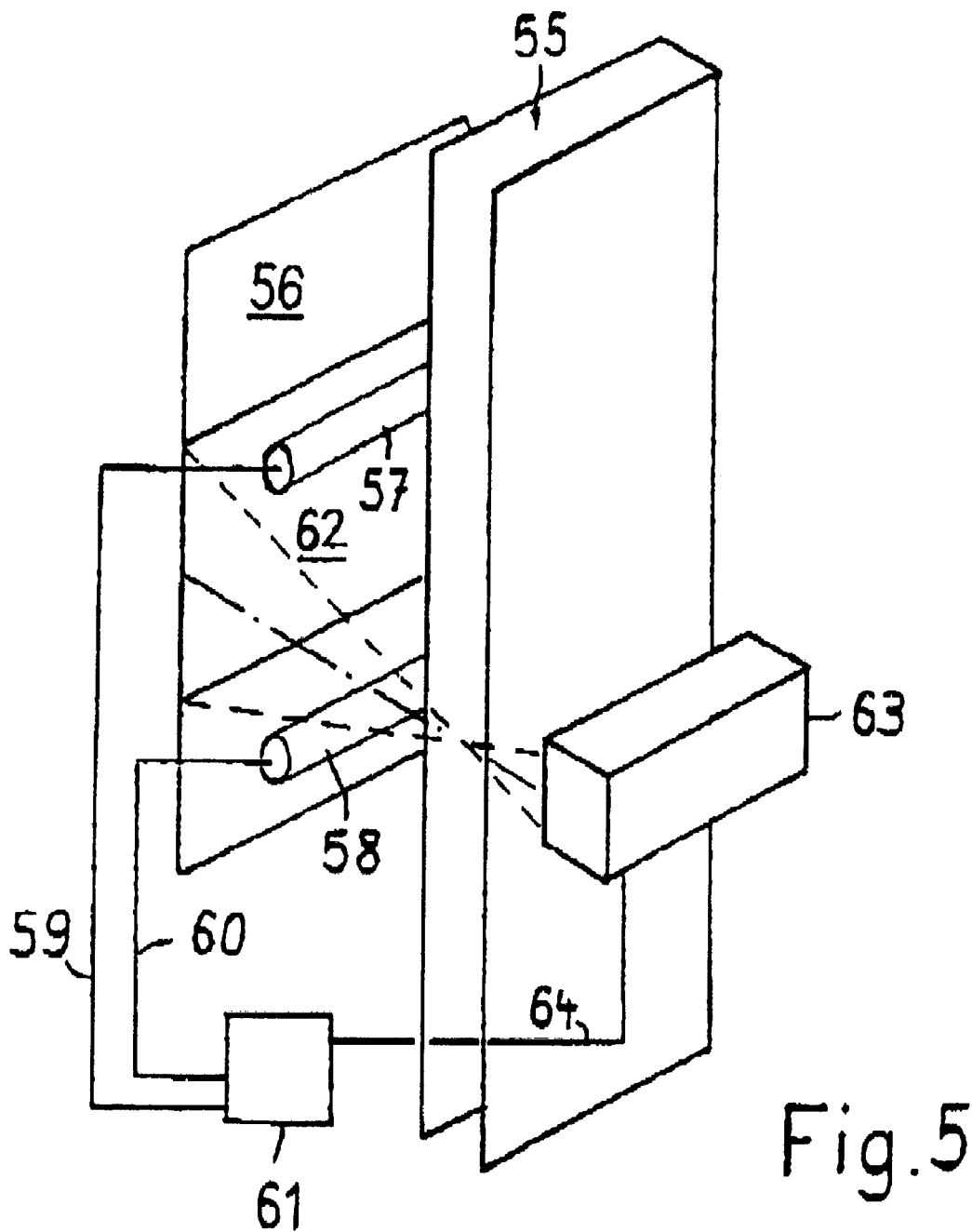

FIG. 5 shows a further construction of the device which, as in FIG. 4,. has only one channel 55 for a loosened flock stream. Here, instead of the channel 36 (FIG. 3), a surface 56 is provided which is illuminated by light sources 57, 58. For controlling the intensity and color of the lighting of the surface 56, said light sources 57, 58 are connected by lines 59, 60 and a controller 61 to one another so that flocks in the channel 55 disappear against said background. This applies particularly to the region of an image 62 which lies in the field of vision of a sensor 63. Here, it is a matter of generating or simulating an image of a collection of textile fibers such as might be seen, for example, in the retaining channel 2. For said purpose, the surface 56, 62 could also take further forms, e.g. it could also receive a projection of an image or be formed by a display screen. A line 64 moreover connects the controller 61 to the sensor 63.

Figure 6:
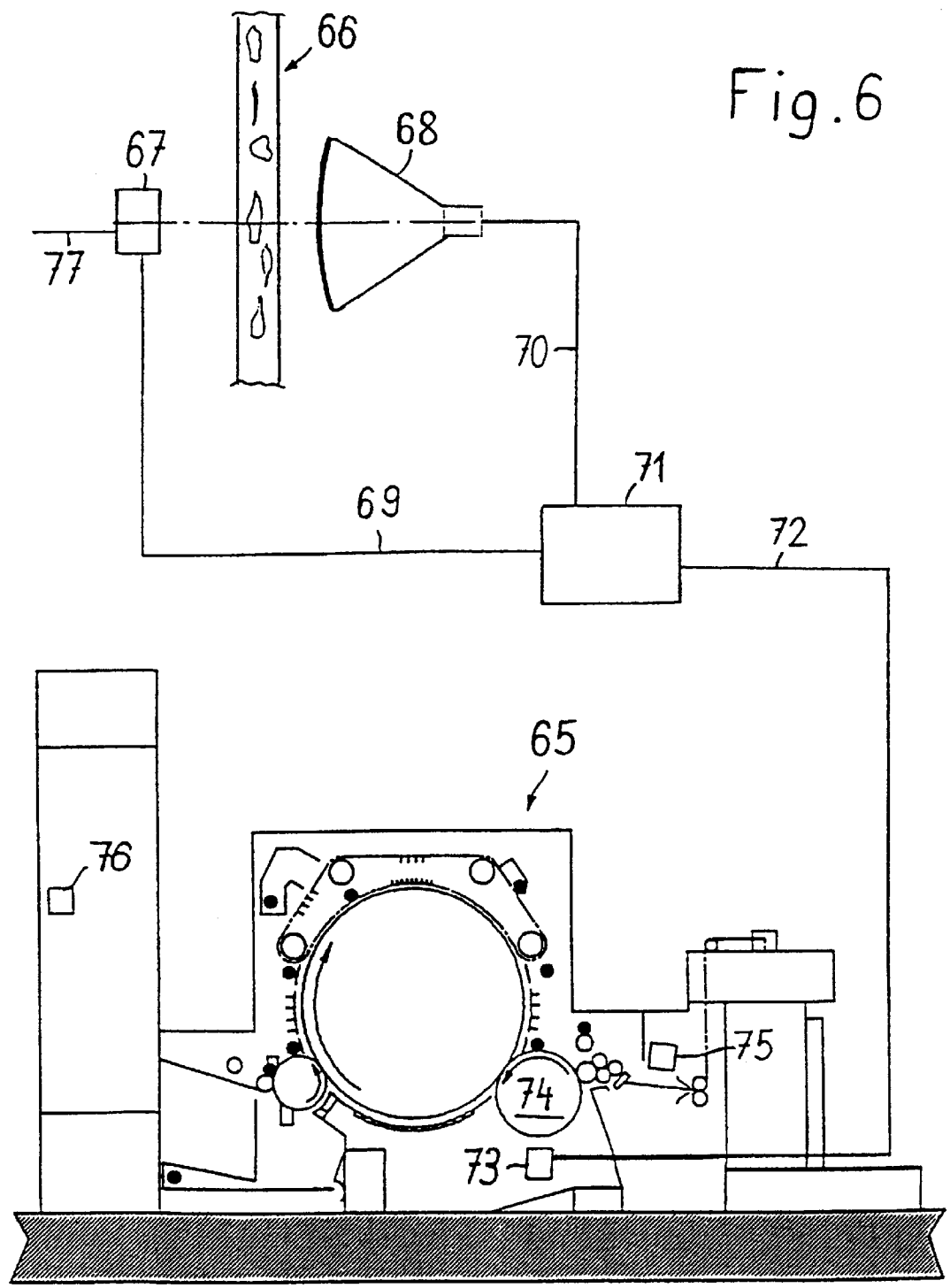

FIG. 6 shows a further construction and application of the invention in connection with a carding machine 65. Provided next to the carding machine 65 there is once more a channel 66 for a loosened flock stream. Said channel 66 preferably lies upstream of the carding machine. A sensor 67 is disposed on one side and a picture tube 68 is disposed on the other side of the channel 66. The sensor 67 and the picture tube 68 are connected by lines 69, 70 to a controller 71, which in turn is connected by a line 72 to a further sensor 73. The latter is disposed, in the present case, in the region of a stripping roller 74 in the carding machine.

There are however additional places where such a sensor might be disposed. They are occupied by sensors 75 and 76. Sensor 75 is provided, for example, in the region of the outgoing fiber fleece, sensor 76 in the retaining chamber.

The mode of operation of the device is as follows: A fiber or flock stream containing impurities is loosened as far as possible so that the flocks are fed as separately as possible in an air stream such as arises in the channels 4, 32, 50, 55, 66. The manner in which the flocks are separated out is known as such and therefore not shown in detail here, except for the cleaning roller 7 in FIG. 1. The fiber or flock stream thus treated is conveyed parallel to, in front of or next to a background and visually inspected, e.g. by a sensor, the background being periodically or continuously adapted to variations of the flock or fiber stream. This is effected in particular to take account of gradually occurring changes in the color or brightness of the fiber or flock stream in that the color or the brightness of the background is adapted to the fiber or flock stream. To guarantee this, the fiber or flock stream is viewed against an adaptable background which preferably comprises the same fiber or flock material. Thus, in the fiber or flock stream there is a first location for measuring or sensing said stream and a second location where said stream acts as a reference quantity or as a background. In the device according to FIG. 1, the first location is to be found in the region 10 and the second location in the retaining channel 2 by the window 13. Here, the two locations are placed in series along the fiber or flock stream. In the device according to FIG. 3, said locations (windows 34 and 37) are disposed next or parallel to one another and the fiber or flock stream is conveyed in two parallel streams. It is preferably to be ensured that the intensity of the lighting is equally high at both locations. For viewing the flock stream, said lighting is to be concentrated on a region around the axis 17 in the object zone 28 (FIG. 2). For the reference quantity or the background 21, the region between light sources 24 and 25 is to be uniformly lit.

In the device according to FIG. 3, a fiber stream 30 consisting of more or less large flocks 33, which for example substantially comprise cotton fibers possibly interspersed with impurities F, is fed in the channel 32. In the channel 36, the flocks or fibers are retained and moved only slowly in a downward direction. In the channel 32, they are moved more quickly in as loose a formation as possible. The purpose of said arrangement is that the retained fibers in front of the window 37 in the channel 36 form a background, which is adapted as time passes, for visual sensing by the sensor 44 of the flocks moving separately through the channel 32.

The same effect may be achieved by an arrangement of channels 2, 4 according to FIG. 1. Unlike the construction according to FIG. 3 where the channel 36 serving as a background and the channel 32 in which the fiber stream is sensed are connected in parallel, here the retaining channel 2 serving as a background is connected in series to the channel 4 for sensing the fiber stream. Furthermore, in said construction, the compressed flocks or fibers 15 are conveyed out of the retaining channel 2 by the feed rollers 5, 6 of a cleaning roller 7, which together with the cutter screen 8 opens the flocks in a known manner. The opened flocks are sucked into the channel 4 where they move in a very separated-out manner past the windows 11, 12 and so maybe viewed from direction 14.

The reference quantity, i.e. the background for the viewed flock stream is therefore adoptively variable because it always corresponds to the color or the image of fibers provided on average. This may alternatively be simulated, in the manner possible with the devices according to FIGS. 4 and 5. According to FIG. 4, the adaptation is simulated in that it may be effected, not continuously, but in discrete steps by exchanging the contents 53 or the container 51. According to FIG. 5, the material too is simulated in that, instead of real textile flocks or fibers with impurities, an image thereof is generated which preferably imitates only mean values of color or brightness of the fibers and flocks. The image preferably shows the same material, e.g. in that it is a picture of the same cotton bale or the same delivery taken by a single sensor or by a camera and projected onto the surface 56. In the simplest case, the surface 56 is lit so brightly by the light sources 57, 58 that the individual flocks in the channel 55, which contain no impurities, do not stand out visually from the surface 56. The luminosity and color of the light sources 57, 58 may be controlled by the controller 61, namely, for example, in such a way that flocks passing in front of the image 62 in the channel 55 do not stand out from the image 62 and that in the image 62 an average color or brightness is generated. A signal from the sensor 63, which passes through the line 64 to the controller 61, adjusts the lighting in such a way that only greater color variations stand out from the image 62 but the lighting is adapted to smaller gradual variations in the fiber stream.

In the construction according to FIG. 6, an—in terms of time and location—averaged color or brightness image of a fiber stream of the kind which may be generated at various points, for example, in a carding machine 65 by a single sensor or a camera is generated in the picture tube 68. The signal from said recording passes through line 72 to the controller 71 and from there through line 70 to the picture tube 68. The sensor 67 therefore detects impurities which stand out from the image in the picture tube 68. Through the line 69 the sensor 67 supplies a signal, which is used for a continuous color or brightness adjustment in the controller 71 and hence corrects the color and luminosity. The basic color adjustment is set once at the sensor 73. Through a line 77 the sensor 67 produces a signal for the removal of impurities.

In conclusion, it should be stated that the signal produced in a sensor by the fiber flocks moving past is evaluated in a manner, which is known as such and therefore not described in greater detail here, and may be used for control of a removal of impurities from the flock stream in the channels 4, 32 in the manner already described in the publications cited in the introduction. The method and the device according to the invention however considerably improve the mode of operation of known sensors.

What is claimed is:

1. Method of detecting impurities (F) in a loosened fiber stream (1) of mainly textile fibers, wherein the fiber stream and at least one reference quantity are sensed using artificial vision at a first location (10), characterized in that said reference quantity (15, 21, 53, 62, 68) is correlated with the fiber stream at least from time to time by taking this reference quantity from the fiber stream (1) itself at a second location (13).

2. Method according to claim 1, characterized in that the reference quantity is disposed in a reference surface (21) and the fiber stream is disposed at a distance from said reference surface in an object zone (28) in the same path of rays (16).

3. Method according to claim 2, characterized in that the object zone (28) is sensed in a clearly defined manner and the reference surface (21) is sensed in an indistinct manner.

4. Method according to claim 2, characterized in that a fiber stream (15, 1) flows in the object zone and in the reference surface.

5. Apparatus for carrying out a method according to claim 1, said apparatus comprising a light permeable channel (4) for a loosened fiber stream (1), and a background that serves as a reference quantity, said background being formed by a channel (2, 36) with fibers (15) retained in it.

6. Apparatus according to claim 5, wherein said light permeable channel for the loosened fiber stream has a first location (10) along the fiber stream, and wherein said channel with the fibers retained in it has a second location (13) along the fiber stream.

7. Apparatus according to claim 6, wherein said first and second locations are disposed in series.

8. Apparatus according to claim 6, wherein said first and second locations are disposed in parallel.

9. Apparatus according to claim 6, wherein said channel for the loosened fiber stream and said channel for the retained fiber stream have windows (34, 35, 37), all of said windows being positioned relative to one another so as to afford a view through the channel (32) for the loosened fiber stream into the channel (36) for the retained fiber stream.

10. Apparatus according to claim 5, wherein said background is formed by an image (62) of a fiber stream on a surface (56).

11. A method for detecting statistically rare impurities in a loosened stream of fibers differing in color from said impurities, said method comprising flowing said stream along a flow channel having transparent walls on opposite sides of a portion thereof;

scanning with an optical system the stream moving through said portion of said flow channel along an optical axis passing through said transparent walls and beyond; and disposing a reference having a color like that of said fibers alongside said portion of said flow channel to intersect said optical axis and provide a background which enhances the color contrast between fibers and impurities.

12. A method according to claim 11, wherein said reference is a body containing said fibers in a more compacted condition than said fibers in said loosened stream.

13. A method according to claim 12, wherein said reference and said mixture of loosened fibers and impurities are parts of a fiber cleaning production line.

14. In apparatus for processing a stream of fibers containing impurities differing in color from the fibers, the improvement which comprises a flow channel along which a mixture of loosened fibers and impurities is moved in an air stream, said channel having a portion provided with transparent walls on opposite sides thereof;

a reference body disposed alongside said portion of said flow channel and having a color like that of said fibers; and an optical system located outside said flow channel for scanning said mixture through said transparent walls along an axis extending across said flow channel and onto said reference body.

15. A combination according to claim 14, wherein said reference body is a mass of said fibers moving along a passage having a transparent wall portion in alignment with said axis of said optical system at a location beyond said flow channel.

16. A combination according to claim 15, wherein said passage is part of a fiber processing line and said flow channel is a later part of the same fiber processing line.

\* \* \* \* \*